(12) United States Patent
Krause et al.

(10) Patent No.: US 8,440,867 B1
(45) Date of Patent: May 14, 2013

(54) PROCESS FOR PRODUCING ETHANOL FROM SYNGAS

(75) Inventors: Theodore R. Krause, Naperville, IL (US); Jerome W. Rathke, Homer Glen, IL (US); Michael J. Chen, Downers Grove, IL (US)

(73) Assignee: U.S. Department of Energy, Washington, DC (US)

( * ) Notice: Subject to any disclaimer, the term of this patent is extended or adjusted under 35 U.S.C. 154(b) by 274 days.

(21) Appl. No.: 12/848,496

(22) Filed: Aug. 2, 2010

(51) Int. Cl.
*C07C 31/02* (2006.01)

(52) U.S. Cl.
USPC .................................................. 568/902.2

(58) Field of Classification Search ............... 568/902.2
See application file for complete search history.

(56) References Cited

U.S. PATENT DOCUMENTS

| | | | | |
|---|---|---|---|---|
| 4,434,248 A | * | 2/1984 | Lin | 518/700 |
| 4,476,334 A | | 10/1984 | Chen et al. | |
| 4,618,628 A | * | 10/1986 | Head et al. | 518/700 |
| 7,375,142 B2 | * | 5/2008 | Pearson | 518/706 |
| 7,718,832 B1 | * | 5/2010 | Hurley et al. | 568/869 |

OTHER PUBLICATIONS

M.J. Chen, Organometallics, vol. 6, No. 9, (1987), pp. 1832-1838.

* cited by examiner

*Primary Examiner* — Brian J Davis
(74) *Attorney, Agent, or Firm* — Bradley W. Smith; Brian J. Lally; John T. Lucas

(57) ABSTRACT

The invention provides a method for producing ethanol, the method comprising establishing an atmosphere containing methanol forming catalyst and ethanol forming catalyst; injecting syngas into the atmosphere at a temperature and for a time sufficient to produce methanol; and contacting the produced methanol with additional syngas at a temperature and for a time sufficient to produce ethanol. The invention also provides an integrated system for producing methanol and ethanol from syngas, the system comprising an atmosphere isolated from the ambient environment; a first catalyst to produce methanol from syngas wherein the first catalyst resides in the atmosphere; a second catalyst to product ethanol from methanol and syngas, wherein the second catalyst resides in the atmosphere; a conduit for introducing syngas to the atmosphere; and a device for removing ethanol from the atmosphere. The exothermicity of the method and system obviates the need for input of additional heat from outside the atmosphere.

18 Claims, 1 Drawing Sheet

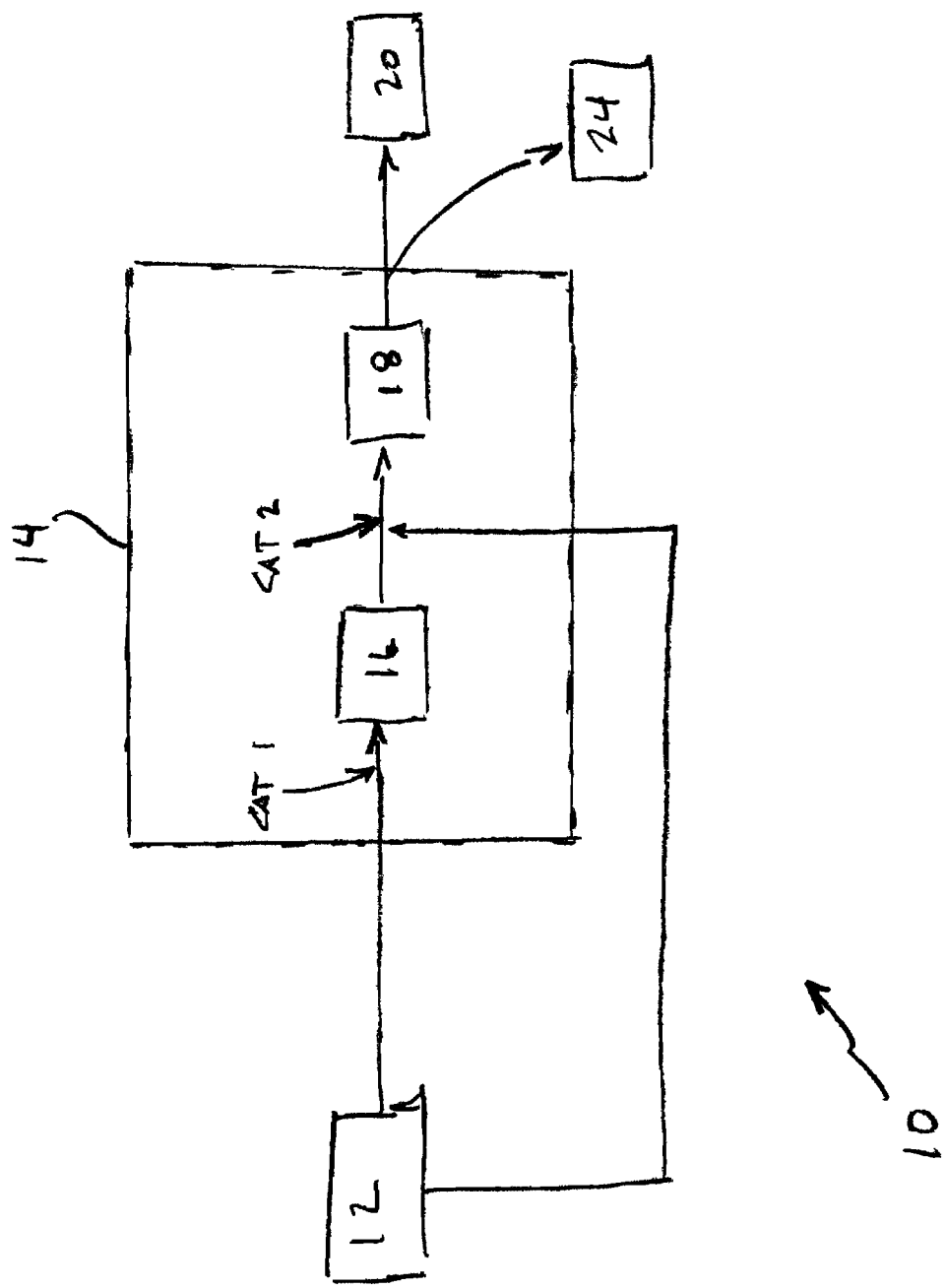

PROCESS FOR PRODUCING ETHANOL FROM SYNGAS

CONTRACTUAL ORIGIN OF THE INVENTION

The U.S. Government has rights in this invention pursuant to Contract No. DE-AC02-06CH11357 between the U.S. Department of Energy and U Chicago Argonne, LLC, representing Argonne National Laboratory.

BACKGROUND OF THE INVENTION

1. Field of the Invention

This invention relates to a method and system for ethanol production, and more specifically, this invention relates to an integrated method and system for producing ethanol from synfuel and methanol feedstocks.

2. Background of the Invention

Ethanol, and the production of ethanol, falls into and out of favor in discussions related to energy independence, national security, and environmental responsibility.

Much of current research focuses on optimizing petroleum feedstock infrastructures by additives for easy incorporation with gasoline, diesel fuel, and jet fuel. However, the natural progression of liquid energy development is toward fuels derived from feedstocks from renewable resources (such as biomass), or solar-based processes.

Biomass-derived fuels include highly oxygenated moieties (e.g. alcohols) and are typically derived from renewable sources and sources comprised mainly of relatively less complex molecules. These sources include wood, paper, and other municipal bio-oriented waste.

Solar based fuels are those produced from carbon dioxide and water using energy. Energy costs to produce solar fuels remain high.

Methanol is a primary transportation fuel. Current methods for producing methanol include the use of catalysts in combination with syn gas. Liquid phase catalysts and solid phase catalysts have been used. Liquid phase processes for producing methanol were developed using coal as a feedstock. Lastly, using natural gas as a feedstock for producing methanol is only technically feasible, given methane's growing importance as a power plant fuel to supplant dirtier coal-fire facilities.

Currently, the primary technology for producing methanol is via the reaction of syngas with a solid phase fixed bed catalyst. This is because liquid entrained methanol catalyst to produce methanol is considered less efficient than solid phase fixed bed catalyst use.

Furthermore, state of the art methanol production sequences are equilibrium limited, which is to say that the presence of methanol often results in the reaction reversing or shifting back to the left. The decomposition of methanol to syn gas (reverse reaction) occurs because the chemistry is limited to the carbon-containing the oxygen atom (single carbon compound). Thus, $H_2$ is lost to form a $CH_2O$, which can then loose $H_2$ to form CO and $H_2$, (i.e., syn gas, the starting reactants). Conversion of syn gas to methanol is significantly limited at relatively low temperatures because of thermodynamics. That is why some processes run under high pressure conditions to "liquefy the product" to drive the reaction to higher conversion. (i.e. Le Chatlier's Principle)

Decomposition of ethanol and higher alcohols also occurs at the oxygen-containing carbon. The alkyl carbons, $CH_3$, in the case of ethanol, tend to react with $H_2$ to form methane during the "reverse" reaction process. As such, the reaction of ethanol to syn gas is essentially irreversible under these reaction conditions.

Also, methanol's drawbacks are formidable and include its toxicity, corrosiveness, and higher volatility.

Ethanol is a safer alternative as a transportation fuel. Ethanol can be derived from synfuels just as methanol. For example, U.S. Pat. No. 4,476,334, held by the instant Assignee, discloses a method for producing ethanol from synfuel by producing methanol or methanol formate as intermediate reactants. However, this process requires that methanol first be produced in a separate step, and then recovered via an energy intensive distillation process. Any ethanol subsequently produced is also separated via distillation.

A need exists in the art for a method and a system for producing ethanol. The method and system should utilize renewable feedstocks such as biomass and municipal solid waste. Further, the method should integrate the chemistry of methanol production to minimize additional capital outlays and energy expenditures.

SUMMARY OF INVENTION

An object of the invention is to provide a method and system for producing ethanol that overcomes many of the disadvantages of the prior art.

Another object of the invention is to provide a method for producing ethanol from syn gas. A feature of the invention is the use of two catalysts, one for purely methanol production, and another for purely ethanol production. An advantage of the invention is that the system integrates methanol with ethanol production, thereby resulting in less energy usage.

Yet another object of the present invention is to provide a system for producing ethanol with methanol as an intermediate. A feature of the system is that the end point production of ethanol is irreversible. An advantage of the system is that the irreversibility continues to drive the conversion of syngas past the intermediate production of methanol to arrive at ethanol.

Still another object of the present invention is to provide a one phase catalyst carrier for use in a process for producing ethanol from syngas. A feature of the invention is the combination of liquid-phase homologation catalyst with solid-phase methanol catalyst, the two catalysts simultaneously residing in the same solvent, oil thereby forming a three-phase catalytic system with catalysts in two different phases. An advantage of this feature is that transfer of methanol moiety to the next step in the reaction occurs in the same reaction phase, thereby streamlining the process.

Briefly, the invention provides method for producing ethanol, the method comprising establishing an atmosphere (e.g. a controlled reaction chamber or space) containing methanol forming catalyst and ethanol forming catalyst; injecting syngas into the atmosphere at a temperature and for a time sufficient to produce methanol; and contacting the produced methanol with additional syngas at a temperature and for a time sufficient to produce ethanol. The exothermicity of the methanol forming step obviates the need for application of heat from outside the atmosphere.

The invention also provides an integrated system for producing methanol and ethanol from syngas, the system comprising: an atmosphere isolated from the ambient environment; a first catalyst to produce methanol from syngas wherein the first catalyst resides in the atmosphere; a second catalyst to product ethanol from methanol and syngas, wherein the second catalyst resides in the atmosphere; a means for introducing syngas to the atmosphere; and a means for removing ethanol from the atmosphere.

BRIEF DESCRIPTION OF DRAWING

The invention together with the above and other objects and advantages will be best understood from the following detailed description of the preferred embodiment of the invention shown in the accompanying drawings, wherein:

FIG. 1 is a schematic depiction of the integrated process, in accordance with features of the present invention.

DETAILED DESCRIPTION OF THE INVENTION

The foregoing summary, as well as the following detailed description of certain embodiments of the present invention, will be better understood when read in conjunction with the appended drawings.

As used herein, an element or step recited in the singular and proceeded with the word "a" or "an" should be understood as not excluding plural said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

The system is a two step, yet single reaction chamber protocol, whereby first methanol is produced and used as a feedstock for ethanol production. The system is an integrated reactor system starting with production of methanol from syngas. The methanol so formed is then reacted with additional syngas in a homologation step, the homologation effected by a transition metal carbonyl catalyst and catalyst promoters, deployed with or without high boiling co-solvent. The system produces ethanol with minimal production of water, higher alcohols and methane.

One embodiment of the process enables higher single-pass conversions of syngas to ethanol at lower operating pressures than those required in sequential reactor systems in which methanol is synthesized in one reactor and then fed into a second reactor for conversion to ethanol. This single pass process utilizes a homogeneous catalyst reaction phase within which methanol- and ethanol-forming catalysts are entrained. Suitable pressures for this embodiment range from about 500 psi to 1,200 psi, with preferable pressures ranging from above about 700 to below 1,000 psi, and ideally at about 750 to 850 psi.

A salient feature of the invention is the combination of methanol forming catalysts with ethanol forming catalysts in the same liquid entrained reactor venue. This combination results in the elimination of energy intensive distillation processes required in state of the art protocols for separating ethanol from the product stream. Rather, the methanol is a reactant toward the production of ethanol, with the formation of ethanol being irreversible. As a result, the reaction, depicted in Equation 1 below, is constantly pulled to the right with methanol serving as the limiting reagent.

A primary advantage of the invented process is that methanol homologation catalyst is co-introduced with methanol catalyst in the same oil phase. This feature provides one reaction venue or phase and as such obviates the need for the just formed methanol to transfer from a first liquid phase (containing the methanol-producing catalyst) to a second phase that contains homologation catalyst.

In the first step of the invented protocol, a solid-phase methanol synthesis is utilized. In one embodiment, syngas ($CO+H_2$) reacts in the presence of fine catalyst particles slurried in a solvent (which is an oil phase), of a three phase slurry reactor system. Suitable oil phase candidates (i.e. solvent for the catalysts) include linear alkanes which are not chemically active under the conditions stated herein. Preferably, the alkane is liquid at room temperature so that it does not solidify when cooled. Also preferably, the alkane has a boiling point temperature high enough so that its vapor pressure at reactions conditions is small to minimize refluxing of the solvent and to keep as much of the solvent in the liquid phase as possible. Suitable nonpolar carriers include, but are not limited to mineral oil, alkanes with carbon numbers above dodecane, and combinations thereof.

Suitable methanol synthesis catalysts comprise a mixture of copper and zinc oxides supported on an alumina support with or without the addition of chemical modifiers, such as chromium oxide, to stabilize the copper oxides. Typical such catalysts are metal oxide catalysts, including but not limited to $CuO$—$ZnO$—$Al_2O_3$, mixed colbalt-molybdenum oxides and combinations thereof. These catalysts are available from Haldor-Topsoe (Houston, Tex.), Johnson-Matthey (Pasadena, Tex.) and Süd-Chemie, Inc. (Houston, Tex.).

Simultaneous with the formation of methanol, suitable homologation catalysts (e.g. $Mn_2(CO)_{10}$) are employed to generate ethanol. The overall process is depicted in Equation 1, below:

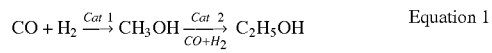

$$CO + H_2 \xrightarrow{Cat\ 1} CH_3OH \xrightarrow[CO+H_2]{Cat\ 2} C_2H_5OH \qquad \text{Equation 1}$$

wherein Cat 1 is the methanol synthesis catalyst and Cat 2 is the homologation catalyst.

Methanol Production
Detail

Prior to methanol production, the catalyst is activated, by being reduced in situ. For example, the cobalt carbony catalysts discussed herein tend to naturally decompose to metal when CO pressure is decreased, but then activated when subjected to the proper ratio of carbon monoxide and hydrogen. The inventors have devised a method for catalyst activation that eliminates the use of reducing gases (either heated or unheated) inasmuch as liquid phase homologation catalysts often reduce down to their metallic states in such envirions. One method of in situ activation devised by the inventors is effected by first mixing both catalysts together in the carrier oil, exposing the oil-entrained methanol- and ethanol-formation catalysts to the reaction atmosphere of CO and $H_2$ at relatively low temperatures (i.e., at or below 100° C.) and then bringing the reactor to the optimal reaction temperature over time (about 1 to 2 degrees per minute) up to the point at which methanol formation is observed. This catalyst activation method provides a means for preventing homologation catalyst from metalizing, sintering and poisoning the also present methanol forming catalyst.

Production of the methanol is carried out at a pressure of between approximately 700 to 750 psi, and between approximately 220-270° C.

Ethanol Production
Detail

The inventors have determined a myriad of ways to effect catalytic homologation of alcohols with synthesis gas. For illustration purposes only, $Mn_2(CO)_{10}$ is discussed herein as the active catalyst for methanol homologation in alkali-metal formate-methanol solutions. Other suitable homologation catalysts are suitable and include $Fe(CO)_5$, $RhI_3$, $Ru_3(CO)_{12}$, and combinations thereof. Suitable catalysts are disclosed in M. J. Chen *Organometallics* Vol 6, No. 9 pp 1832-38 (1987), and also in U.S. Pat. No. 4,476,334,the entirety of both the paper and the patent which is incorporated herein by reference.

The homologation catalysts are utilized and are present simultaneously with the initial methanol producing catalysts, in a slurry based liquid phase.

Homologation occurs at a range of temperatures and pressures. In situations whereby $Mn_2(CO)_{10}$ catalyst is utilized, temperatures from about 225 to 275° C. and syngas pressures from about 750 to 2500 psi are suitable.

FIG. 1 is a schematic drawing of the invented system, designated as numeral 10. A feedstock of the system is syngas 12, the latter of which is derived from the thermal treatment (e.g. gasification) of coal, biomass, municipal solid waste, or other carbonaceous material. Generally, oxygen concentrations during gasification process range between approximately 0 percent and 20 volume percent of the total reaction atmosphere, and preferably 7 and 15 volume percent of the total reaction atmosphere, and most preferably less than 7 volume percent of the total reaction atmosphere. Given a particular carbonaceous waste feedstock, the oxygen levels are empirically determined to arrive at the preferred stoichiometric ratio of carbon monoxide to hydrogen in the syngas. A suitable ratio would be about one part carbon monoxide to two parts hydrogen gas.

Upon gasification of that biomass feedstock, the syngas ($CO+H_2$) is directed to an integrated reactor 14 containing catalyst for both methanol and ethanol production. In one embodiment of the invention, the integrated reactor is pressurized to at least about 725 psi. Pressures of up to 1450 psi are suitable. Inasmuch as the reactions are highly (approximately 90.8 kJ/kg-mol) exothermic, the reactor (and the atmosphere defined by the void formed by the reactor) does not need to be heated once methanol production begins. Preferably, the feed gases are heated to the reaction temperature of 225-275° C., which is generally below the range at which homologation catalyst starts losing its stability. In one embodiment, the feed gases are heated to between 225-275 C prior to their introduction into the atmosphere. After such introduction, the exothermicity of the reaction obviates the need for any application of heat from outside the system.

Chemically, the ethanol production occurs after, or downstream of, the methanol production, even though for the purposes of industrial production, ethanol forms simultaneously with the formation and consumption of methanol. In light of the foregoing, both catalysts 1 and 2 are present together as part of a homogenous reaction liquor. Relegating the reaction venue to a homogeneously mixed liquor (i.e. where the catalysts are mixed together and throughout the venue) eliminates the need of solid catalyst supports, which would otherwise cause sintering of catalyst constituents, leading to catalyst inactivity. Also, use of a homogeneous liquid eliminates the potential for undesirable Fischer-Tropsch synthesis occurring which would convert carbon monoxide to more complex petroleum-like molecules instead of the methanol intermediate and ethanol final products.

The reaction liquor further comprises organic fluids such as organic liquid solution. The organic liquid solution may include methanol, metal carbonate, metal bicarbonate of the alkali or alkaline earth metals, methyl formate, and combinations thereof. A source of methyl formate is the reaction of methanol with carbon monoxide from the syngas. The alkali or alkaline earth moieties are provided to increase basicity of the solution and therefore stabilize the metal carbonyl catalyst as a nucleophilic transition agent capable of undergoing methylation. Trace amounts of reaction by-products including acetaldehyde, acetals, methyl acetate, and ethyl formate may also be present in the liquor.

The formation of higher alcohols (i.e. higher than ethanol) is avoided because the homologation reaction process becomes significantly slower as the formate intermediate grows in carbon number, i.e. methyl formate reacts considerably faster than ethyl formate, which reacts faster the propyl formate, etc. Thus the invented reaction "stops" at ethanol. In fact, a salient feature of the invention is the use of methanol and ethanol catalysts that produce only methanol and ethanol respectively.

The immediate consumption of methanol to form ethanol eliminates drawbacks of state of the art methanol production schemes. A feature of the present invention is that the presence of homologation catalyst in close spatial relationship to the methanol forming catalyst results in conversion of the methanol simultaneous with creation of the methanol.

The need for comparatively less water in the instant protocol means less need for distillation of final liquor. This is because the invented process produces more $CO_2$ and less $H_2O$ as its sacrificial oxygen-removal product, as depicted in Equations 2 and 3, below:

$$CH_3OH + 2CO + H_2 \rightarrow CH_3CH_2OH + CO_2 \qquad \text{Equation 2}$$

$$CH_3OH + 2CO + 2H_2 \rightarrow CH_3CH_2OH + H_2O \qquad \text{Equation 3}$$

Removing oxygen via $CO_2$ production is a feature of the process inasmuch as it is less energy intensive to remove carbon dioxide via distillation. The invented process allows methanol to be produced with minimal water by-products.

Ethanol 20 is removed from the reaction atmosphere through a suitable chemical separation process. A feature of the invention is that ethanol is removed via the operation of a single distillation train instead of the two distillation train process disclosed in U.S. Pat. No. 4,476,334, which is owned by the instant assignee, the entirety of which is incorporated by reference.

It is to be understood that the above description is intended to be illustrative, and not restrictive. For example, the above-described embodiments (and/or aspects thereof) may be used in combination with each other. In addition many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the terms "comprising" and "wherein." Moreover, in the following claims, the terms "first," "second," and "third," are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

The embodiment of the invention in which an exclusive property or privilege is claimed is defined as follows:

1. A method for producing ethanol, the method comprising:
    establishing an atmosphere containing a methanol forming catalyst and an ethanol forming catalyst;
    injecting syngas into the atmosphere at a temperature and for a time sufficient to produce methanol; and
    contacting the produced methanol with additional syngas at a temperature and for a time sufficient to produce ethanol.

2. The method as recited in claim 1 wherein the methanol forming catalyst and the ethanol forming catalyst reside in the same liquid phase.

3. The method as recited in claim 1 wherein the methanol forming catalyst produces only methanol and the ethanol forming catalyst produces only ethanol.

4. The method as recited in claim 1 wherein oxygen is removed via the creation of carbon dioxide.

5. The method as recited in claim 1 wherein the methanol forming catalyst is $CuO-ZnO-Al_2O_3$ and the ethanol forming catalyst is $Mn_2(CO)_{10}$.

6. The method as recited in claim 2 wherein the methanol forming catalyst and the ethanol forming catalyst are homogeneously mixed together throughout the liquid phase.

7. The method as recited in claim 1 wherein the syngas comprises a CO and $H_2$ weight ratio of between 1:1 and 1:3.

8. The method as recited in claim 1 wherein the atmosphere is maintained at between about 225° C. and 275° C.

9. The method as recited in claim 1 wherein the atmosphere is maintained at between about 750 psi and 2,500 psi.

10. The method as recited in claim 1 wherein the syngas is heated prior to its injection into the atmosphere and no additional heat is applied to the atmosphere from outside the atmosphere.

11. An integrated system for producing methanol and ethanol from syngas, the system comprising:
    an atmosphere isolated from the ambient environment;
    a first catalyst to produce methanol from syngas wherein the first catalyst resides in the atmosphere;
    a second catalyst to produce ethanol from methanol and syngas, wherein the second catalyst resides in the atmosphere;
    a means for introducing syngas to the atmosphere; and
    a protocol for separating ethanol from the atmosphere.

12. The system as recited in claim 11 wherein the atmosphere is hermetically sealed from the natural atmospheric pressure, natural temperature, and natural humidity of the ambient environment.

13. The system as recited in claim 11 wherein the first catalyst and the second catalyst reside in a single liquid phase.

14. The system as recited in claim 11 wherein the first catalyst is a copper-zinc chromite and the second catalyst is a combination of $Mn_2(CO)_{10}$ and $KCHO_2$.

15. The system as recited in claim 11 wherein the protocol for separating ethanol is a distillation train.

16. The system as recited in claim 11 further comprising a means for heating the syngas to between 225° C. and 275° C. prior to its introduction into the atmosphere.

17. The system as recited in claim 11 wherein the system operates at between 700 and 2,500 psi.

18. The system as recited in claim 16 wherein no heat is added to the system after the heated syn gas is fed to the atmosphere.

* * * * *